United States Patent [19]

Guadalupi et al.

[11] 4,092,358

[45] * May 30, 1978

[54] PROCESS FOR THE PRODUCTION OF UREA HAVING A LOW CARBAMATE CONTENT

[75] Inventors: Mario Guadalupi, Milan; Umberto Zardi, San Donato Milanese, both of Italy

[73] Assignee: Snamprogetti S.p.A., Milan, Italy

[*] Notice: The portion of the term of this patent subsequent to Apr. 8, 1992, has been disclaimed.

[21] Appl. No.: 733,716

[22] Filed: Oct. 18, 1976

Related U.S. Application Data

[60] Continuation of Ser. No. 529,120, Dec. 3, 1974, abandoned, which is a division of Ser. No. 260,339, Jun. 6, 1972, Pat. No. 3,876,696, which is a continuation of Ser. No. 756,845, Sep. 3, 1968, abandoned.

[51] Int. Cl.² .......................................... C07C 126/00
[52] U.S. Cl. ............................................... 260/555 A
[58] Field of Search ......................................... 260/555

[56] References Cited

U.S. PATENT DOCUMENTS

| | | | |
|---|---|---|---|
| 2,848,493 | 8/1958 | Dewling et al. | 260/555 |
| 3,301,897 | 1/1967 | Cook | 260/555 |
| 3,356,723 | 12/1967 | Kaasenbrood | 260/555 |
| 3,406,201 | 10/1968 | Bauman et al. | 260/555 |
| 3,514,484 | 5/1970 | Wentworth | 260/555 |
| 3,530,180 | 9/1970 | Giommi | 260/555 |
| 3,711,544 | 1/1973 | Summerville | 260/555 |
| 3,816,528 | 6/1974 | Cook | 260/555 |
| 3,867,442 | 2/1975 | Logemann | 260/555 |
| 3,876,696 | 4/1975 | Guadalupi et al. | 260/555 |

FOREIGN PATENT DOCUMENTS 1,031,529  6/1966  United Kingdom ............... 260/555

Primary Examiner—Earl C. Thomas
Assistant Examiner—Eugene T. Wheelock
Attorney, Agent, or Firm—Morgan, Finnegan, Pine, Foley & Lee

[57] ABSTRACT

The improvement in the process for production of urea wherein carbon dioxide and excess ammonia are reacted in a synthesis zone producing a solution of urea contaminated with ammonium carbamate which is decomposed in a decomposer having a pressure lower than the pressure in the synthesis zone which comprises allowing the solution which passes into the decomposer to flow as a thin film over a surface heated to an extent sufficient to cause at least a part of the ammonium carbamate to decompose into gaseous carbon dioxide and ammonia, the latter recycled to the synthesis zone.

4 Claims, 1 Drawing Figure

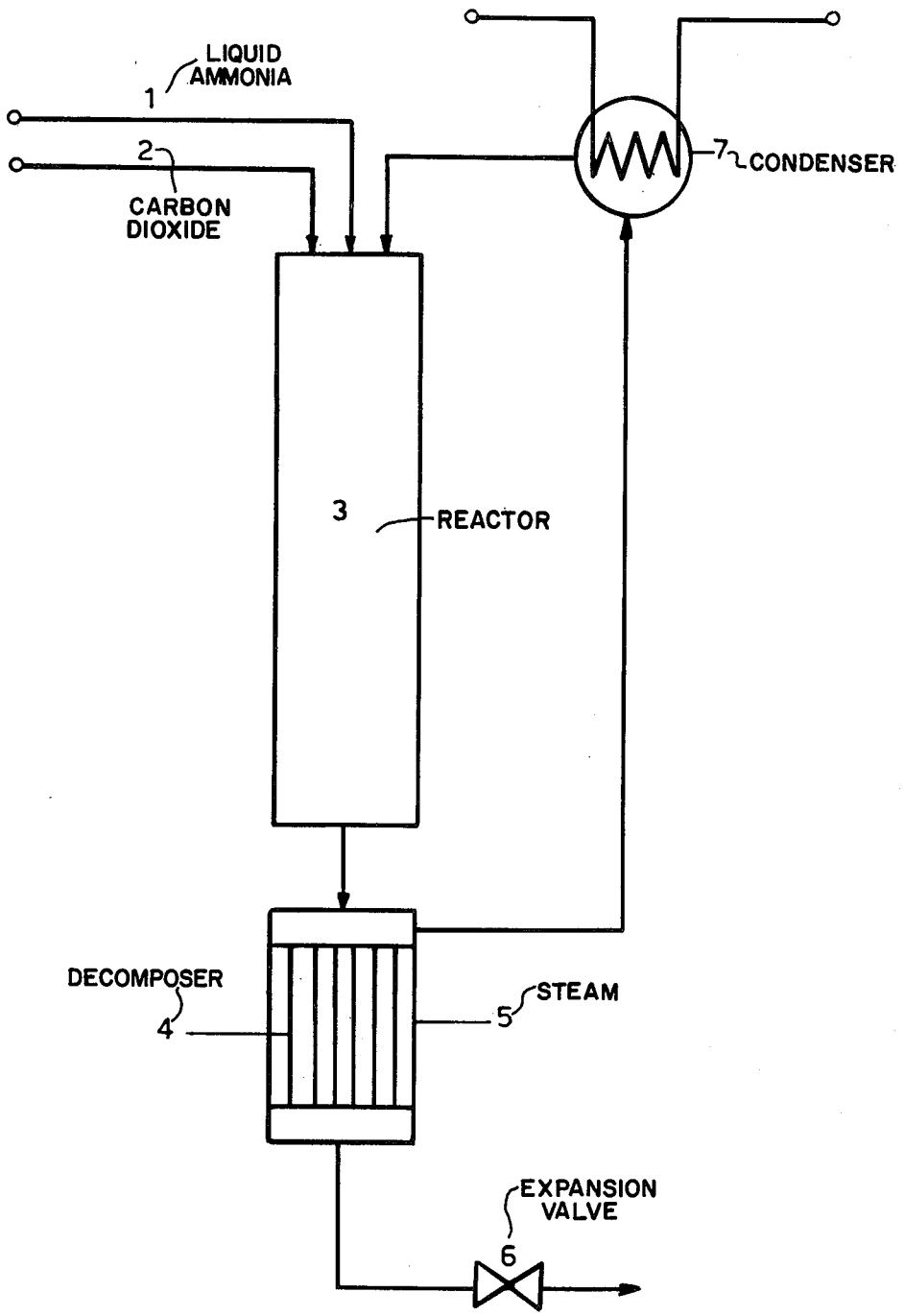

PROCESS FOR THE PRODUCTION OF UREA HAVING A LOW CARBAMATE CONTENT

This is a continuation of application Ser. No. 529,120 filed Dec. 3, 1974, now abandoned, which in turn is a division of application Ser. No. 260,339 filed June 6, 1972 (U.S. Pat. No. 3,876,696) which in turn is a continuation of Ser. No. 756,845, filed Sept. 3, 1968 now abandoned. su This invention relates to a process for the production from ammonia and carbon dioxide of urea having a low ammonium carbamate content.

It is known that in the production of urea from carbon dioxide and ammonia relatively large amounts of ammonium carbamate are formed. The presence of the ammonium carbamate calls for the provision of expensive cycles for the conversion of the carbamate into urea, and in addition, the contaminated urea cannot be used for certain purposes, for instance in agriculture.

According to the known processes, the contaminating carbamate which has been formed may be either recycled to the synthesis reactor to be converted into urea, (but such recycle involves technical problems), or decomposed into ammonia and carbon dioxide by thermal splitting in the presence or absence of an excess of one of the two reactants (i.e. either ammonia or carbon dioxide), which are then recycled to the synthesis reactor.

It is an object of the present invention to provide a process for producing urea having a low carbamate content by subjecting the synthesis product to a novel treatment.

According to the present invention, there is provided a process for the production of urea, which comprises feeding carbon dioxide and an excess of ammonia to a synthesis zone in a reactor, reacting the carbon dioxide and ammonia therein so as to produce, as the reaction product, a solution of urea contaminated with ammonium carbamate and containing the excess ammonia, causing or allowing the said solution to flow as a thin film over a surface heated to an extent sufficient to cause at least part of the ammonium carbamate decompose into gaseous carbon dioxide and ammonia, recycling the decomposition products as well as the excess ammonia to the synthesis zone, and recovering the urea solution having a reduced ammonium carbamate content.

By using the process of the present invention, without employing expensive decomposers or expensive recycles, it is possible to obtain urea having a low carbamate content corresponding to from 10 to 30% of the percentage obtained when using conventional processes.

The residual carbamate does not present any difficulty and it may be split into urea in a simple known way, for instance reducing the pressure.

Thus the production, according to the present invention, of urea with a low carbamate content is simple and economically convenient, it being only necessary to provide a surface down which the urea solution coming from the synthesis zone of the reactor is allowed to drop as a thin liquid film, while at the same time the heat transfer necessary for the carbamate splitting takes place.

The formation of the thin liquid film may be obtained, for example, by allowing the reaction product to drop at a suitable rate along the inside wall of a heat exchanger connected to the reactor of along the wall of a part of the reactor other than the synthesis zone.

The thin film may be decomposed at temperatures and pressures lower than those of the synthesis, for example 150°–200° C. lower than the synthesis temperature and from 30 to 80 atmospheres lower than the synthesis pressure, or, preferably, at the same conditions as those occuring in the urea synthesis, so that the decomposition products can be recycled without further energy consumption. The process of the present invention may be applied to any process of urea production, particularly to syntheses effected at a temperature of from 150° to 350° C. and at a pressure of from 100 to 300 atmospheres.

It is critical that the urea synthesis is effected with an ammonia excess based on the stoichiometric proportions, and consequently that the solution coming out of the synthesis zone of the reactor contains some dissolved ammonia; this fact is easy to achieve since in order to obtain high conversions, the synthesis is usually carried out with an ammonia/carbon dioxide ratio of from 2.3:1 to 5.5:1.

For a better understanding of the present invention and to show how the same may be carried into effect, reference will now be made, by way of example, to the accompanying drawing which is a diagrammatic representation of an apparatus suitable for carrying out the process of the present invention.

Referring now to the drawing, there is shown a synthesis reactor 3 having a liquid ammonia inlet pipe 1 and a carbon dioxide inlet pipe 2. The products of the synthesis are passed as a solution to a decomposer 4 consisting of a tube nest heat exchanger, where the solution is allowed to flow over the heating surfaces at the same conditions of pressure and temperature as those in the reactor 3. To maintain the surfaces at the desired value, heat is given to the surfaces over which the thin film is passed by contacting the surfaces with steam introduced through a pipe 5.

Urea solution having a reduced carbamate content is recovered from the bottom of the decomposer 4 and the solution is passed through an expansion valve 6, whereafter it may be used in its existing form or subjected to further treatment.

The decomposition products, namely carbon dioxide and ammonia, pass out of the top of the decomposer 4 and are condensed in a condenser 7 and recycled to the reactor 3.

The invention will now be illustrated by the following Example.

EXAMPLE

Ammonia and carbon dioxide were fed into a synthesis section at a temperature of 180° C. and at a pressure of 150 atmospheres, the molar ratio of ammonia/carbon dioxide being equal to 3. A 55% conversion into urea was obtained, based on the carbon dioxide fed to the synthesis section, and the urea had a carbamate content of 48% based on the total amount of carbamate and urea. The reaction product was then allowed to flow along the surface of a thin film heat exchanger at the same temperature and pressure as those of the synthesis.

The recovered urea possessed an 8% carbamate content, based on the total amounts of carbamate and urea.

The remaining carbamate can be removed by any known process to obtain a urea solution substantially free of carbamate.

What we claim is:

1. In a process for the production of urea which comprises feeding carbon dioxide and an excess of ammonia to a synthesis zone at temperatures from 150° to 350° C and at pressures from 100 to 300 atmospheres, reacting the carbon dioxide and ammonia therein at an ammonia/carbon dioxide mole ratio of from 2.3:1 to 5.5:1 to produce, as the reaction product, a solution of urea contaminated with ammonium carbamate and containing the excess ammonia, passing said solution directly into a decomposer having a pressure lower than the pressure in said synthesis zone, withdrawing gaseous carbon dioxide and ammonia from the upper part of the decomposer, recycling said gaseous carbon dioxide and ammonia as well as the excess ammonia to the synthesis zone as a liquid and recovering the urea solution;

the improvement which comprises allowing said solution which passes into the decomposer to flow as a thin liquid film over a surface heated to an extent sufficient to cause at least a part of the ammonium carbamate to decompose into gaseous carbon dioxide and ammonia wherein only decomposition products carbon dioxide and ammonia and excess ammonia, materials formed or contained in the decomposer, are recycled to the synthesis zone.

2. The process according to claim 1 wherein the temperature in said decomposer is the same or lower than the temperature in said synthesis zone.

3. The process according to claim 1 wherein the pressure in said decomposer is from 30 to 80 atmospheres lower than the pressure in said synthesis zone.

4. The process according to claim 1 wherein the decomposer is connected to the synthesis zone in a single reactor.

* * * * *